United States Patent [19]

Bonner, Jr.

[11] 4,062,363
[45] Dec. 13, 1977

[54] CATHETER

[76] Inventor: Francis J. Bonner, Jr., 1240 Conshohocken State Road, Gladwyne, Pa. 19035

[21] Appl. No.: 594,097

[22] Filed: July 8, 1975

Related U.S. Application Data

[63] Continuation-in-part of Ser. No. 404,400, Oct. 9, 1973, Pat. No. 3,894,540.

[51] Int. Cl.² .......................................... A61M 25/00
[52] U.S. Cl. .................................. 128/349 R; 128/348
[58] Field of Search ............... 128/349 R, 348, 349 B, 128/349 BV, 351, 214.4; 206/63.2 R, 63.2 A, 364

[56] References Cited

U.S. PATENT DOCUMENTS

| 1,120,549 | 12/1914 | Schellberg | 128/349 R |
|---|---|---|---|
| 3,154,080 | 10/1964 | Rowan et al. | 128/349 R |
| 3,421,509 | 1/1969 | Fiore | 128/349 R |
| 3,444,860 | 5/1969 | Harrell | 128/349 R |
| 3,556,294 | 1/1971 | Walck | 128/349 R X |
| 3,592,192 | 7/1971 | Harautuneian | 128/214.4 |
| 3,854,483 | 12/1974 | Powers | 128/349 R |
| 3,861,395 | 1/1975 | Taniguchi | 128/349 R |
| 3,894,540 | 7/1975 | Bonner, Jr. | 128/349 R |
| 3,898,993 | 8/1975 | Taniguchi | 128/349 R |

Primary Examiner—Aldrich F. Medbery
Attorney, Agent, or Firm—Seidel, Gonda & Goldhammer

[57] ABSTRACT

A catheter is provided, having a flexible elongated conduit adapted for insertion into a passage in the patient's body. The conduit has a forward insertion end and a rearward distal end, and has a handpiece which surrounds a portion of the conduit in the area of the insertion end. A sealing envelope is attached forwardly on the handpiece and is sealed with respect to the conduit, forming a sealed, enclosed space surrounding at least a portion of the handpiece and also surrounding at least a portion of the conduit. The exterior surface of the rearward portion of the handpiece provides a support for forward sliding manipulation of the envelope, by the individual who inserts the conduit into the body passage of the patient.

25 Claims, 2 Drawing Figures

CATHETER

RELATED APPLICATION

This is a continuation-in-part of my co-pending application Ser. No. 404,400, filed Oct. 9, 1973, now U.S. Pat. No. 3,894,540, granted July 15, 1975.

BRIEF DESCRIPTION OF THE INVENTION

This invention relates to a catheter having special construction features which greatly facilitate the manipulative act of catheterization of the patient. More particularly, this invention relates to a catheter having an elongated conduit which is adapted to be inserted into a body passage such as the urinary urethra or the trachea, and which has a flexible sheath, envelope or shield, all of which are generically referred to herein as an envelope, protecting the patient against invasion of microorganisms such as bacteria or the like, during the act of catheterization. Still further, this invention relates to a catheter of the urinary type which can be much more readily used in the catheterization procedure than catheters of the prior art.

In some instances a catheter of the intermittent type is prescribed, in which situation the catheter may be subjected to a single use and then discarded. The catheter according to this invention is much easier to manipulate and to use than catheters of the prior art. In other situations, the catheter is allowed to remain within the patient's body for several days or more, with substantially continuous drainage of body fluid into a collecting bag or the like. This invention relates to catheters of this so-called "indwelling" type, which are highly advantageous manipulatively and otherwise in connection with the indwelling application.

DISCUSSION OF THE PRIOR ART

As has been pointed out in my aforesaid co-pending application, one of the most serious problems in the use of catheters, particularly indwelling urinary catheters, is the problem of infection. When a urinary catheter is allowed to remain in the patient's bladder for a period as long as four days or more, substantially every patient contracts a bladder infection, particularly when the patient is situated in a hospital environment. Serious infections also occur in intermittent use of catheters.

The catheter described in my aforesaid co-pending application Ser. No. 404,400 is highly advantageous whether used as an intermittent catheter or as an indwelling catheter, in that the operative length of the catheter tube is sealed to inhibit invasion of foreign micro-organisms and thus maintains a substantially sterile condition on the entire operative surface of the catheter tube. This is accomplished by sealing the outer surface of the catheter tube with respect to a surrounding sheath, such seal acting against invasion of foreign micro-organisms. In the use of the catheter of my aforesaid co-pending application Ser. No. 404,400, the catheter tube is longitudinally slidable relative to the sheath for insertion into the body passage of the patient, and at least a portion of the sheath is retractable without interfering with the integrity of the protective seal. Accordingly, the operative length of the catheter tube which is to be inserted into the patient's body is protected from bacterial invasion through the sheath, during the period of insertion and the period of use.

It is an object of this invention to provide a catheter which may readily be used by the attending physician or even by the patient himself or herself, without subjecting the patient to any substantial risk of infection, and with particular ease of manipulation.

Another object of this invention is to provide a catheter wherein the surface of the catheter tube that is to be inserted into the patient's body is completely protected from bacterial invasion, not only during the period of insertion but also during the period of actual use.

The U.S. Pat. No. 3,854,483 to Powers, granted Dec. 17, 1974, discloses a catheter having an introducer end portion which is adapted to be administered by a nurse. In the use of such a catheter, the introducer end portion is inserted approximately three eighths of an inch into the urethra, and a nurse holds the introducer and grasps the catheter tube itself through a surrounding polyethylene sheath. In this manner, the catheter tube is gently slidably moved outward from the introducer, into the urethra and ultimately into the bladder. According to the disclosure of the Powers patent, a water-soluble lubricant is provided, ahead of the end of the catheter, so that the catheter tube ejects the lubricant from a passageway in the introducer as the catheter tube is moved through the introducer and into the patient's urethra, In this manner, the catheter tube is moved through the passageway so that the sterile lubricant is ejected from the introducer into the patient's urethra as the catheter tube is inserted therein, the catheter tube pushing the lubricant from the introducer simultaneously with the insertion of the catheter tube into the urethra.

It is an object of this invention to provide a catheter which can be manipulated much more easily than any of the catheters of the prior art, and which does not depend upon the ability of the person performing the catheterization procedure to utilize fine hand movements in grasping and controlling, and pushing, the rather flexible and elongated catheter tube itself.

Other objects and advantages of this invention, including the simplicity of the same and the ease of its operation, will further become apparent hereinafter and in the drawings, of which:

FIG. 1 is a view in longitudinal section of a particular form of catheter embodying features of this invention, showing the catheter partially inserted into the urethra at an early stage of the catheterization procedure; and FIG. 2 is an enlarged view showing important structural details in the vicinity of the forward and rearward ends of the catheter of FIG. 1, and showing the catheter further inserted into the urethra in a further stage of the catheterization procedure.

DETAILED DESCRIPTION OF THE INVENTION

Figure 1:
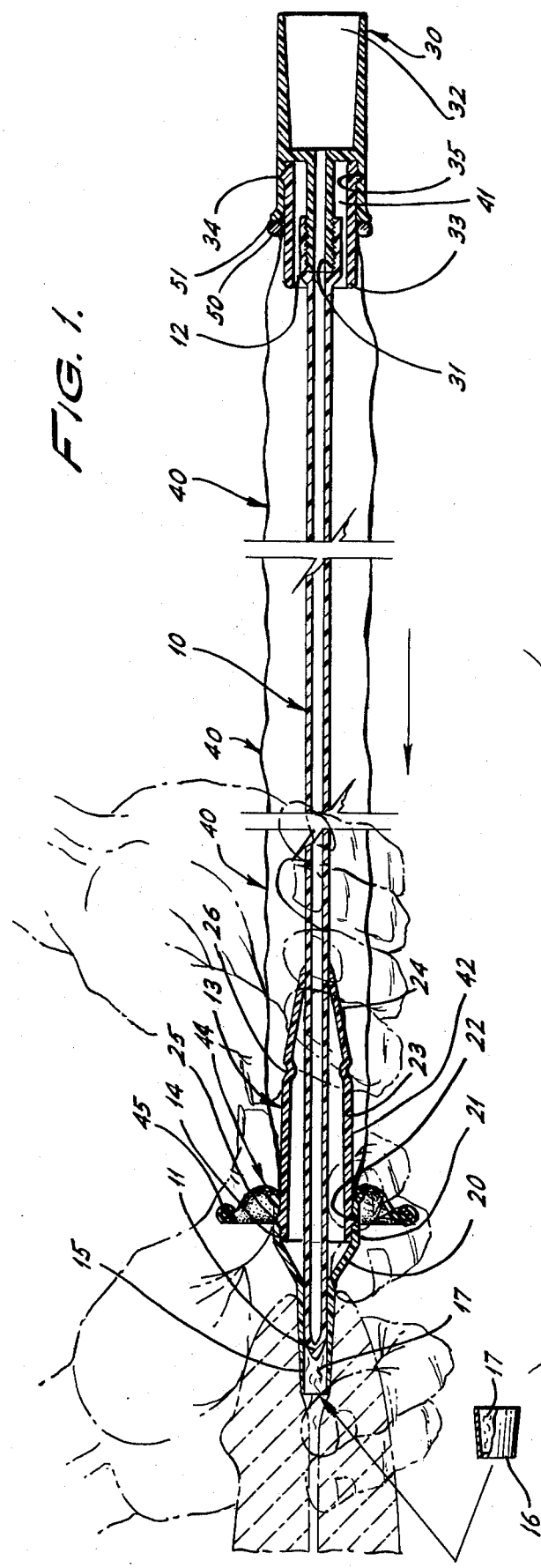

In the description that follows, specific terms will be used in describing a specific form of the catheter, as shown in the drawings. The use of such specific terms is not intended to limit the scope of this invention, which is defined in the appended claims.

Turning now to FIG. 1 of the drawings, the number 10 designates a flexible conduit which has the shape of an elongated tube, usually made of rubber or plastic, which is intended to be inserted into a passage in the patient's body, such as insertion into the urethra or trachea, for example. The catheter is shown in FIG. 1 in a straightened arrangement for the sake of convenience of illustration; in actual practice it bends somewhat under the influence of gravity because of its flexibility. The flexible conduit 10 has an insertion or forward end 11 and a distal or rearward end 12 through which the body fluid is discharged.

The number 13 comprehensively designates a handpiece having a forward end portion 14 having, at its insertion end, a dilator 15 which is in the form of a tube of reduced cross-section with respect to the cross-section of the handpiece 13, which extends forwardly of the forward end of the conduit 10, receiving the conduit 10 longitudinally slidably within the bore of the tube comprising the dilator 15. As shown in FIG. 1, the dilator tube 15 extends forwardly of the forward end of the conduit 10, and a cap 16 is shown in closely-fitting, sliding arrangement with the outer surface of the dilator 15. A slug of lubricant 17 is desirably located within the end portion of the dilator 15, for lubricating the forward end portion of the conduit 10 during the catheterization procedure, and for injection into the urethra ahead of the catheter tube, if desired.

As shown in FIG. 1, the forward end portion 14 of handpiece 13 has a conical portion 20 which is inclined upwardly and rearwardly, terminating in a further, slightly inclined but generally cylindrical terminal portion 21. An internal groove 22 extends around the inside surface of the terminal portion 21 of the forward end portion 14 of the handpiece 13.

The handpiece 13 also includes a generally cylindrical body portion 23 having a rearwardly downwardly inclined conical portion 24, the latter having a reduced diameter at its rearward end and having a closely-engaged sliding fit with the conduit 10. The conduit 10, thus slidably gripped at the rear and at the forward portions of the handpiece 13, has capacity for longitudinal sliding movement with respect to the handpiece 13 for insertion into the body passage in the catheterization procedure.

The body portion 23 has a circumferentially extending ridge 25 which mates with the internal groove 22 in order to secure the forward end portion 14 with respect to the body portion 23.

A further circumferential groove 26 is provided around the outside surface of the handpiece 13, at approximately the juncture between the body portion 23 and the conical portion 24, for a purpose which will further become apparent hereinafter.

At its rearward end the conduit 10 is secured to a rearward fitting 30, which has a forwardly extending tube 31 which fits snugly within the distal end of the conduit 10. The rearward fitting 30 has a large diameter tube portion 32 formed integrally with the forwardly extending tube 31, and providing an enlarged passageway which provides for the disposition of the fluid removed by the catheterization procedure. As shown, the enlarged passageway 32 is ideally constructed to serve as a bag adaptor, for utilization in conjunction with the fluid collecting bag which is particularly useful when the catheter is subjected to indwelling use.

The rearward fitting 30 also includes a cylindrical tube portion 33 which is larger than but substantially concentric with the forwardly extending tube 31, and which is provided with a circumferentially extending ridge 34 mating with a corresponding responding groove 35 formed in the enlarged tube portion 32. In this manner the tube 33 may be snap-fitted to the tube portion 32.

It will accordingly be apparent that the catheter tube 10 is fixedly secured to the rearward fitting 30, but is longitudinally slidable with respect to the handpiece 13 which is located at the forward end of the conduit 10.

It is important in accordance with this invention to seal the operative length of the catheter to inhibit invasion of foreign micro-organisms and to protect the outer surface of the conduit which is to be inserted into the patient's body passsge in such a manner that the catheter tube is protected from bacterial invasion during the period of insertion and the period of use. Novel means have been provided for accomplishing this important result, as will now be described in detail hereinafter.

A protective envelope 40 is shown in FIG. 1 as extending substantially the entire operative length of the catheter tube 10, and the envelope 40 is sealed substantially at the forward end of the body portion 23, and is also sealed at the rearward end of the catheter, to the rearward fitting 30. As specifically shown in FIG. 1, the envelope 40 extends between the internal groove 22 in the terminal portion 21 of the forward end portion 14 of the handpiece 13, and the ridge 25 of the body portion 23. This is a snap-fit, generating high local pressures within the interfitting portions themselves, and thus tightly sealing the envelope 40 against the invasion of foreign micro-organisms such as bacteria and the like, and also forming a strong anchoring means for the envelope, which has advantages which will further become apparent hereinafter.

Similarly, at its rearward end, the envelope 40 is pinched between the ridge 34 and the groove 35. This arrangement, again, provides a high local pressure in a manner to pinch the envelope 40 tightly between the tube 33 and the enlarged tube 32, assuring the integrity of the seal against invasion of micro-organisms such as bacteria or the like. It also forms a mechanically strong connection which is of importance in the operation of the catheter while performing the catheterization procedure.

The envelope 40 is preferably constructed of a thin, lightweight material, flexible enough to gather upon itself many times. While it may be transparent, this is not a necessary requirement. However, the material of the envelope 40 should be tear-resistant and should have a reasonably substantial tensile strength, for reasons which will appear in further detail hereinafter.

It will accordingly be appreciated that, as shown in FIG. 1, the flexible elongated conduit 10, which is adapted for insertion into the body passage, is strongly sealed with respect to a longitudinally gatherable and retractable envelope which is strongly sealed to the handpiece 13 at a location forward of the rearward end of the handpiece. These seals are so tight as to inhibit invasion by foreign micro-organisms. Further, the envelope 40 is also sealed to the conduit 10 rearwardly of the handpiece (as shown in FIG. 1, to a rearward fitting 30) to provide a sealed, enclosed space 41 surrounding at least a portion of the conduit 10. It will further be appreciated that the exterior surface 42 of the handpiece 13 provides a support for forward sliding and gathering movement of the envelope 40 concurrently with insertion of the conduit 10 into the body passage of the patient, as will further become apparent hereinafter. The handpiece 13 and its dilator portion 15, accordingly, are preferably composed of substantially rigid materials — or the handpiece at least has sufficient rigidity to form a substantial base upon which the envelope 40 can be guided.

Still referring to FIG. 1 of the drawings, the number 44 designates a supplemental rolled flexible sheath, which is preferably composed of a stretchable material such as rubber or the like, and which is sealed in the same manner as the forward end of the protective envelope 40, between the groove 22 and the ridge 25. This supplemental flexible sheath is rolled upon itself as indicated at 45 and, when used in the catheterization of a male patient, may be unrolled over the surface of the penis in a manner to effect a further seal against the invasion of micro-organisms such as bacteria and the like.

Although FIG. 1 does not show a bag sealed to the bag adaptor 32, it will be understood and appreciated that for indwelling use the bag and the catheter are supplied as an integral unit, sealed and sterilized. Preferably, catheters according to this invention whether used as intermittent catheters or as indwelling catheters, are delivered in a sealed envelope containing a notice that the contents are sterile.

Figure 2:
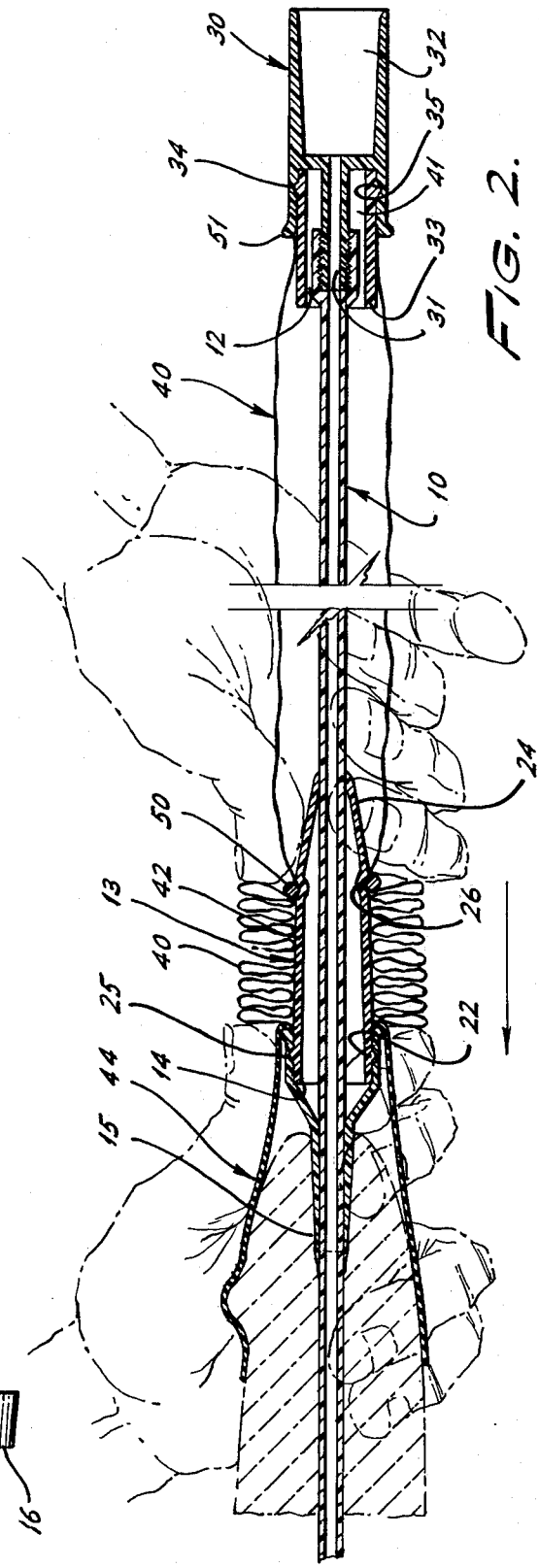

In the performance of the catheterization procedure utilizing the catheter appearing in FIG. 1, after first having thoroughly scrubbed the areas surrounding the urethra, the physician removes the catheter from its protective envelope, removes the cap 16, and inserts the dilator 15 into the patient's body passage, such as the male or female urethra. In male catheterization, one hand of the physician (as shown in dash lines in FIG. 1) grasps the penis in the palm of the hand and the thumb and first two fingers of the same hand grasp the handpiece 13 in a pinch grip. Holding the forward end of the handpiece 13 firmly, and placing the other hand upon the outer surface of the envelope 40 at a location in the area of the outer surfaces 42 of the handpiece 13, the physician then simply shifts the protective envelope 40 itself in a forward direction as shown in FIG. 2. This applies tension to the envelope 40, which applies a forwardly directed force to the rearward fitting 30, which applies a forwardly directed force to the catheter tube 10, which causes the catheter tube to tend to slide forwardly with respect to the handpiece 13. By taking successive short lengths of the protective envelope 40, and by successively sliding these short lengths forwardly along the outer surfaces 42 of handpiece 13, as shown in FIG. 2, successive lengths of catheter tube 10 are progressively advanced within the urethra or other body passage, and in this manner, the introduction of the catheter tube 10 is continued stepwise until it has reached the desired position. Preferably, one or both of the sections 14 and 23 of the handpiece 13 are quite rigid so that they may be managed even by a patient whose neuromuscular control or skeletal alignment is poor, without substantially bending or kinking the conduit 10. Since the protective envelope 40 has an appreciable tensile strength and since it is flexible enough to be bunched up or gathered in the area of the handpiece 13, as shown in FIG. 2, it serves ideally as a means for applying a forwardly directed force to the catheter tube or conduit 10 itself.

When the catheter of FIG. 1 is intended for intermittent use, the usual practice, after all the desired fluid has been drained from the patient's body, it is quite simple to withdraw the conduit 10 gently but directly from the patient's body. The catheter may be discarded or cleaned, resterilized and reused.

It will be appreciated, of course, that for indwelling use, after draining fluid as above, the supplemental rolled flexible sheath 44 may be unrolled, with the rolled portion 45 extending over the outer surface of the penis as shown in FIG. 2, in a manner to serve as a protective sheath against bacterial invasion in indwelling use.

The number 50 designates an elastic ring which, when not in use, is conveniently housed within the space provided by the enlarged lip 51 of the tube 32 as shown in FIG. 1. However, as is shown in FIG. 2 of the drawings, when the catheter tube 10 has been inserted into the patient's body, and when it is desired to maintain the tube in that predetermined position in the patient's body, the elastic ring 50 may be rolled forwardly over the outer surface of the protective envelope 40 and may be seated in the lock groove 35, thus pinching the envelope 40 in position, and preventing the rearward movement of the catheter tube 10. This is an important and advantageous feature of this invention when the catheter is intended for indwelling use.

Although the handpiece 13, and particularly the portions 23 and 24 thereof, may have a wide variety of shapes, including a rearward end portion which is cylindrical or which has a square, triangular or polygonal cross-section, it is important in accordance with this invention to provide the supporting outer surfaces 42 in such a manner that the individual performing the catheterization procedure can easily and gently slide the envelope 40 in a forward direction, over the surface 42. While the body portion 23 may be cylindrical, and while the conical portion 24 need not always be conical, it is highly preferred to provide the body portion 23 with a slight inclination inwardly toward the rear, and to provide the portion 24 in the form of a cone which is gently inwardly rearwardly inclined. It is important that the rear end of the conical portion 24 may be rounded and desirable that it be in close contact with the catheter tube 10, in order to prevent the envelope 40 from inadvertently being pinched between the two, in the course of the catheterization procedure. This, of course, is also avoided by manipulating the envelope 40 in such a manner that finger contact is maintained in the area of the supporting surfaces 42, 42, while maintaining the envelope 40 under tension as the catheter tube 10 is advanced into the urethra.

The seal that is formed between the handpiece and the forward end of the envelope preferably has sufficient mechanical strength (as in the form shown in the drawings) to form an anchoring means against which the thin, flexible envelope may be gathered, as shown in FIG. 2.

Although various forms of snap fitting seals have been disclosed herein and are shown in the drawings, it will be apparent that seals of a wide variety of other forms may be used instead, including seals formed by adhesion or welding or the like, provided however that the adhesion or welding must be continuous in a manner to form a seal protecting against contamination by the invasion of pathogenic or other micro-organisms such as bacteria, for example.

Accordingly, it will be appreciated that the catheter in accordance with this invention has solved the problem of ease of use in the catheterization procedure while maintaining optimum resistance to the problem of infection. As stated, such infection is usually the result of contamination of the urinary catheter with pathogenic micro-organisms.

Usually, such contamination occurs either by contamination of the catheter by the individual inserting the catheter, by contamination of the catheter by the patient receiving the catheter (micro-organisms living in the distal part of the urethra), or by contamination of the external wall of a catheter which is indwelling. In the latter case, the most common source of infection is the patient's own perineum followed by the bed clothes, and by the attending staff which manipulates the catheter. Infection may also occur from infected urine which has been extruded into an urinary collection device and remains attached to a catheter.

In accordance with this invention, infection is substantially precluded notwithstanding the potential sources of contamination referred to above.

In the past, closed systems have consisted of indwelling catheters having a tubular extension that is adjoined to the catheter itself. Studies have shown that bacteria can migrate from the bag up the wall of the catheter to reach the bladder. Such migration is effectively prevented in accordance with this invention.

A further point which is relevant to this invention is the fact that bacteria capable of causing disease live in the distal urethra. These bacteria are often pushed into the bladder with the introduction of the catheter. The catheter equipped with the meatal dilator described in this specification markedly reduces this occurrence since the meatal dilator contacts and covers the area involved and insulates it from the catheter tube which is introduced into the bladder.

It has also been demonstrated that, in devices of the prior art, bacteria can migrate up the external wall of the catheter reaching the bladder by way of the urethra. In accordance with this invention the migration of bacteria up the external wall of the catheter tube 10 is effectively prevented by the integrity of the seals at the ends of the protective envelope 40.

Further, although various anchoring devices may be used for anchoring the catheter to the penis, equivalent devices may be applied, such as a vaginal dilator, in the female.

It will be appreciated that various alternate forms of collecting devices may be used for the fluid, and that antiseptic material may be contained within the collecting bag. Time-release capsules may be used, so that antiseptic or bactericidal or bacteriostatic materials can be released at various points in time.

In using catheters according to this invention, many patients are enabled to employ self-catheterization which, in rehabilitation medicine, is frequently the most desirable.

It will be appreciated that catheters in accordance with this invention are useful for other uses than urinary catheters. For example, they can be used for tracheal aspiration as in the case, for example, of a patient who has had a tracheotomy where his respirations are embarrassed by excess secretions. In such a situation the patient has difficulty coughing up, because of the open tracheotomy tube, and therefore excess fluids need to be suctioned out. Catheters in accordance with this invention are ideally suited for that purpose, and their capability of preventing bacterial infection is an important factor in such use.

Although this invention has been described with reference to specific forms thereof, it will be appreciated that many variations may be made without departing from the spirit and scope of this invention. For example, certain parts may be reversed and certain features may be utilized independently of other features. Further, equivalent elements may be substituted for those specifically shown and described, all within the spirit and scope of this invention as defined in the appended claims.

The following is claimed:

1. A catheter comprising a flexible elongated conduit adapted for insertion into a body passage, said conduit having a forward insertion end and a rearward distal end spaced rearwardly from said insertion end, a handpiece surrounding a portion of said conduit in the area of said insertion end, said handpiece having a forward end and a rearward end, said conduit portion being longitudinally slidably positioned within said handpiece, means forming a longitudinally retractable envelope, sealing means sealing said envelope to said handpiece at a location spaced forwardly of said rearward end of said handpiece, with a portion of said envelope free of said handpiece rearwardly of said seal, said envelope also being sealed to said conduit rearwardly of said handpiece to provide a sealed, enclosed space surrounding at least a rearward position of said handpiece which is located rearwardly of said seal, and said envelope also surrounding at least a portion of said conduit, the exterior surface of said rearward portion of said handpiece comprising a substantially cylindrical body portion for providing a gathering support for the longitudinally retracted portion of the envelope, and a ramp-like conical portion sloping to adjacent the surface of the conduit for supporting forward sliding movement of said envelope concurrently with insertion of said conduit into said body passage.

2. The catheter defined in claim 1, wherein said handpiece includes a body portion having a predetermined cross-section, and having, at its forward end, a dilator portion having a smaller cross-section than the cross-section of said handpiece.

3. The catheter defined in claim 2, wherein said flexible conduit has an outside diameter substantially equal to the inside diameter of said dilator.

4. The catheter defined in claim 2, wherein said body portion and said dilator portion are separate pieces sealed to one another.

5. The catheter defined in claim 2, wherein the forward end of said envelope is sealed at the juncture of said dilator portion and said body portion.

6. The catheter defined in claim 4, wherein a supplemental rolled flexible sheath is sealed at the juncture of said dilator portion and said body portion.

7. The catheter defined in claim 5, wherein a supplemental rolled flexible sheath is sealed to said envelope at the juncture of said dilator portion and said body portion.

8. The catheter defined in claim 1, wherein said portion of said handpiece which is located rearwardly of said seal has a rearwardly inwardly inclined rearward portion.

9. The catheter defined in claim 8, wherein said inclined rearward portion is substantially conical in shape.

10. The catheter defined in claim 1, wherein said handpiece is substantially cylindrical.

11. The catheter defined in claim 1, wherein said handpiece is substantially conical in shape.

12. The catheter defined in claim 1, wherein said handpiece includes on its outer surface an anchoring groove, and wherein an elastic ring is provided outside said envelope and engagable with said groove through said envelope to anchor at least a portion of said envelope in position relative to said handpiece.

13. The catheter defined in claim 12, wherein a fitting is provided in the area of said rearward distal end of said conduit, wherein said envelope is sealed to said fitting, and wherein said elastic ring is adapted to be positioned outside said envelope but supported through said envelope by said fitting.

14. The catheter defined in claim 1, wherein a fitting is provided in the area of said rearward distal end of said conduit, said fitting comprising a plurality of tube pieces having a snap fit between them, and wherein said envelope is sealed to said fitting within said snap fit.

15. The catheter defined in claim 14, wherein one of said tube pieces includes an inner portion which is sealed to the distal end of said conduit.

16. The catheter defined in claim 14, wherein one of said tube portions is arranged to support said elastic ring and wherein the other of said tube portions has an outwardly flared forward end portion the end of which has a diameter approximately equal to that of said elastic ring, thereby forming a lock for said elastic ring.

17. The catheter defined in claim 1, wherein said envelope comprises a thin, flexible material and wherein said handpiece comprises a substantially rigid material, said envelope being slidably gatherable upon the rearward portion of said handpiece.

18. The catheter defined in claim 17, wherein said sealing means sealing said envelope to said handpiece includes anchoring means forming a mechanical stop against which said envelope may be gathered.

19. In a method of catheterizing a patient with protection against invasion by foreign micro-organisms, wherein said catheter is as defined in claim 1 and includes a catheter tube, a handpiece and a flexible envelope, the step which comprises advancing said catheter tube within the urethra by displacing said envelope forwardly along the rearward portion of said handpiece.

20. The method defined in claim 19, further including the steps of applying a tension force to said envelope and applying said tension force to said catheter tube to advance said catheter tube within said urethra.

21. The method defined in claim 19, wherein said handpiece also includes a dilator portion at the front end thereof through which said catheter tube is longitudinally movable, the further steps of inserting said dilator portion into a portion of said urethra, and advancing said catheter tube along said dilator portion by shifting said envelope forwardly along the rearward portion of said handpiece.

22. The method defined in claim 19, wherein said envelope has flexibility affording repeated gathering upon itself, and wherein said step of displacing said envelope includes the step of incrementally shifting said envelope forwardly along said handpiece.

23. The method defined in claim 19, wherein said envelope has flexibility affording repeated gathering upon itself, and wherein said step of displacing said envelope includes the step of repeatedly gathering said envelope upon itself.

24. The method defined in claim 22, further including the step of repeatedly gathering said envelope on said rearward portion of said handpiece.

25. The method defined in claim 19, further including the step of securing said envelope to said handpiece after insertion of said catheter tube.

* * * * *